United States Patent [19]

Takahashi et al.

[11] Patent Number: 5,266,463

[45] Date of Patent: Nov. 30, 1993

[54] HIGHLY SENSITIVE ASSAY METHOD FOR L-CARNITINE AND COMPOSITION FOR PRACTICING SAME

[75] Inventors: Mamoru Takahashi; Shigeru Ueda, both of Shizuoka, Japan

[73] Assignee: Asahi Kasei Kogyo Kabushiki Kaisha, Osaka, Japan

[21] Appl. No.: 640,117

[22] Filed: Jan. 11, 1991

[30] Foreign Application Priority Data

Jan. 11, 1990 [JP] Japan ................................. 2-4063
Nov. 9, 1990 [JP] Japan ............................... 2-305439

[51] Int. Cl.$^5$ .......................... C12Q 1/32; C12P 19/36
[52] U.S. Cl. ...................................... 435/26; 435/89; 435/90; 435/117; 435/128; 435/829; 436/815
[58] Field of Search .................... 435/26, 89, 90, 117, 435/128, 829; 436/815

[56] References Cited

U.S. PATENT DOCUMENTS

| | | | |
|---|---|---|---|
| 3,964,974 | 6/1976 | Banauch et al. ...................... | 435/26 |
| 4,221,869 | 9/1980 | Vandecasteele et al. ............ | 435/117 |
| 4,598,042 | 7/1986 | Self ........................................ | 435/26 |
| 4,650,759 | 3/1987 | Yokozeki et al. .................... | 435/128 |

OTHER PUBLICATIONS

"A Simple Fluorometric Method for the Determination of Serum Free Carnitine", by K. Watanabe et al., pp. 315-318.
"A Method for the Fractionation and Determination of Carnitines in Milk and Milk Products", by M. Hamamoto et al., pp. 389-395.
"Quantitative Bestimmung von L-Carnitin mit Hilfe von Carnitin-dehydrogenase aus Pseudomonas putida", by W. Schopp et al., pp. 285-289.
"An Improved and Simplified Radioisotopic Assay for the Determination of Free and Esterified Carnitine", *Journal of Lipid Research*, vol. 17, 1976, by J. McGarry et al., pp. 277-281.
"A Method for the Determination of Carnitine in the the Picomole Range", Clin. *Chim. Acta*, vol. 37, 1972, by G. Cederblad et al., pp. 235-243.
"Enzymological Determination of Free Carnitine Concentrations in Rat Tissues", *Journal of Lipid Research*, vol. 5, 1964, by N. Marquis et al., pp. 184-187.
"Properties of Partially Purified Carnitine Acetyltransferase", *The Journal of Biological Chemistry*, vol. 238, No. 7, Jul. 1963, By I. Fritz et al., pp. 2509-2517.
Schopp et al., *European J. Biochem.*, vol. 10, pp. 56-60, 1969.
Aurich et al., *European J. Biochem.*, vol. 6, pp. 196-201, 1968.
Matsumoto et al., *Clin. Chem.*, vol. 36, No. 12, pp. 2072-2076, 1990.

*Primary Examiner*—Michael G. Wityshyn
*Assistant Examiner*—Abdel A. Mohamed
*Attorney, Agent, or Firm*—Young & Thompson

[57] ABSTRACT

A method of assaying L-carnitine in a specimen comprises reacting a specimen containing L-carnitine with:

a) L-carnitine dehydrogenase having coenzymes of the thio-NAD group and of the NAD group, and which catalyzes a reversible reaction forming dehydrocarnitine from a substrate of carnitine,
b) $A_1$ and
c) $B_1$ to effect a cycling reaction of the formula

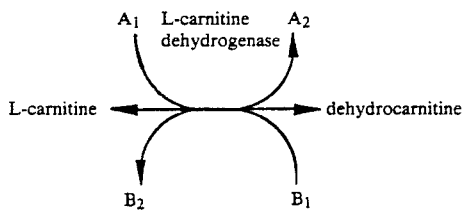

wherein $A_1$ is thio-NAD group or NAD group, $A_2$ is a reduced form of $A_1$, when $A_1$ is thio-NAD group, $B_1$ is reduced NAD group and when $A_1$ is NAD group, $B_1$ is reduced thio-NAD, and wherein $B_2$ is an oxidized form of $B_1$; and measuring an amount of $A_2$ or $B_1$ generated or consumed by the cycling reaction. A composition for performing the assay comprises the above L-carnitine dehydrogenase, as well as the above components $A_1$ and $B_1$.

10 Claims, 2 Drawing Sheets

HIGHLY SENSITIVE ASSAY METHOD FOR L-CARNITINE AND COMPOSITION FOR PRACTICING SAME

FIELD OF THE INVENTION

This invention relates to a highly sensitive assay method for L-carnitine, especially L-carnitine contained in a specimen, and to a composition for assaying L-carnitine

BACKGROUND OF THE INVENTION

L-carnitine is an essential substance for mediating long-chain fatty acid transport through the mitochondrian membrane prior to intracellular β-oxidation, and hence a deficiency of L-carnitine causes disorders in fatty acid and its related metabolisms. particularly, it is believed that disorders of the skeletal muscle and cardiac muscle, both of which are high energy consumption tissues depending on carnitine and lacking in carnitine generation, occur from such deficiency. Heretofore a disease arising from inborn irregularities of carnitine metabolism has been studied, however in recent time, secondary disorders of carnitine metabolism have become a problem in patients suffering from nephrosis and undergoing dialysis. Carnitine is administered to carnitine-deficient patients who have a disease of the body muscle or cardiac muscle, or to patients undergoing dialysis. Studies on the behavior of carnitine in disease and therapy have been required, however a desirable assay method for carnitine in the clinical field has not been developed.

Known assay methods for carnitine are as follows:

1. L-carnitine and acetyl CoA are treated with carnitine acetyltransferase (CAT), and the thus-liberated CoASH and 5,5'-dithio-bis-2-nitrobenzoate (DTNB) are further reacted to generate thiophenolate ion which is colorimetrically measured (DTNB method). This method is described in *J. Biol. Chem.*, Vol. 238, p. 2509 (1963), *J. Lipid Res.*, Vol. 5, pp. 184-187 (1964) and *Clinical Pathology*, Vol. 36, N. 11, pp. 1296-1302 (1988).

2. L-carnitine and $^{14}C$- or $^{3}H$-labelled acetyl CoA are treated with CAT to generate labelled acetyl-L-carnitine and CoASH, and radioactivity is measured (radioisotope method). This method is described in *Clin. Chem. Acta*, Vol. 37, pp. 235-243 (1972), *J. Lipid Res.*, Vol. 17, pp. 277-182 (1976), and *J. Japan. Nut. Food. Soc.*, Vol. 41, N. 5, pp. 389-395 (1988).

3. L-carnitine and NAD are treated with L-carnitine dehydrogenase to generate 3-dehydrocarnitine and NADH, and increased UV absorption of NADH is measured (carnitine dehydrogenase method). This method is described in *Eur. J. Biochem.*, Vol. 6, pp. 196-201 (1968), ibid. Vol. 10, pp. 56-60 (1969), and *Fresenius Z. Anal. Chem.*, Vol. 320, N. 3, pp. 285-289 (1985).

4. L-carnitine and acetyl CoA are treated with CAT to generate CoA which is reacted with n-{p-(2-benzimidazolyl)-phenyl)-malimide (BIPM), and fluorescent intensity of the resulting CoA-BIPM is measured (fluorescence method). This method is described in *Ann. Rep. MHW Institute for Nerve Disease*, pp. 315-318 (1986).

In the prior art, the DTNB method and the fluorescence method require a deproteinization treatment in an assay of serum L-carnitine, which is a complex operation. The radioisotope method has an advantage in its sensitivity and specificity, however special facilities are required for measuring radioactivity. The carnitine dehydrogenase method has a disadvantage due to the small molecular absorption coefficient of NADH, i.e. $\epsilon = 6.22$ (cm$^2$/μmol) at 340 nm, and hence it is difficult to assay serum carnitine in a patient disease involving carnitine deficiency (*Neurology*, 25:16-24 (1975)), and, moreover, the generated NADH is partially consumed by another dehydrogenase pre-existing in serum, such as lactate dehydrogenase, which causes an error in measurement.

We previously invented an assay method of L-carnitine, in which formazan generated in an enzymatic reaction with L-carnitine dehydrogenase was quantitatively measured (Jap. Pat. Appln. No. 1-196550). This method has, however, the disadvantage of insufficient sensitivity for a small amount of serum collected from a premature infant, such as an amount of 20 μl, as compared with a relatively large amount of serum from an adult.

Under these circumstances, it has been desired to develop an advantageous method for assaying L-carnitine without any need for complex treatment such as deproteinization or for special facilities, and which is able to measure even a trace amount of serum L-carnitine taken from a premature infant.

SUMMARY OF THE INVENTION

We have studied a reaction system using L-carnitine dehydrogenase (EC 1.1.1.108), and found that, in a reversible reaction in which dehydrocarnitine is generated from a substrate of L-carnitine, when a reaction system, wherein dehydrocarnitine is generated from L-carnitine with a coenzyme of NAD group together with another trace amount NADH group of coenzyme, was subjected to reversible cycling reaction between L-carnitine and dehydrocarnitine, a linear increase in the generated amount of NADH group was observed over time, and further that an increasing rate thereof is in proportion to an amount of L-carnitine or dehydrocarnitine in the sample.

We have further found that in the said enzymatic cycling reaction, when thionicotinamide adenine dinucleotide group (hereinafter designated thio-NAD group) or reduced thio-NAD group (hereinafter designated thio-NADH group) is used as a NAD group or NADH group, and an amount of change in any of the coenzymes is measured depending upon a difference in a maximum absorption of NADH group at approx. 340 nm and that of thio-NADH group at approx. 400 nm, an amount of L-carnitine or dehydrocarnitine in the sample can be most precisely measured.

OBJECTS OF THE INVENTION

An object of the present invention is to provide a highly sensitive assay method for L-carnitine, which comprises reacting a specimen with reagents containing (1) L-carnitine dehydrogenase having coenzymes of thionicotinamide adenine dinucleotide group (hereinafter designated thio-NAD group) and nicotinamide adenine dinucleotide group (hereinafter designated NAD group) and which catalyzes a reversible reaction forming essentially dehydrocarnitine from a substrate of L-carnitine, (2) A$_1$ and (3) B$_1$ to construct a cycling reaction of the formula

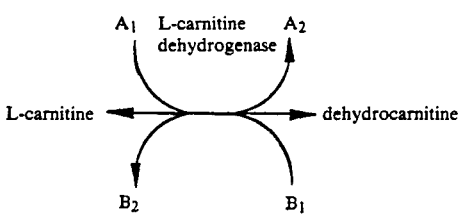

wherein $A_1$ is thio-NAD group of NAD group, $A_2$ is a reduced form of $A_1$, when $A_1$ is thio-NAD group, $B_1$ is reduced NAD group and when $A_1$ is NAD group, $B_1$ is reduced thio-NAD, and $B_2$ is oxidized form of $B_1$. An amount of $A_2$ or $B_1$ which depends on the above reaction is then measured.

Another object of the present invention is to provide a composition for assaying L-carnitine consisting essentially of the following components (1)–(3):

(1) L-carnitine dehydrogenase which has coenzymes of thionicotinamide adenine dinucleotide group (hereinafter designated thio-NAD group) and nicotinamide adenine dinucleotide group (hereinafter designated NAD group) and which catalyzes a reversible reaction forming essentially dehydrocarnitine from a substrate of L-carnitine, (2) $A_1$ and (3) $B_1$ wherein A is thio-NAD group or NAD group, when $A_1$ is thio-NAD group, $B_1$ is reduced form of NAD group, and when $A_1$ is NAD group, $B_1$ is reduced form of thio-NAD group.

DETAILED DESCRIPTION OF THE INVENTION

Figure 1:
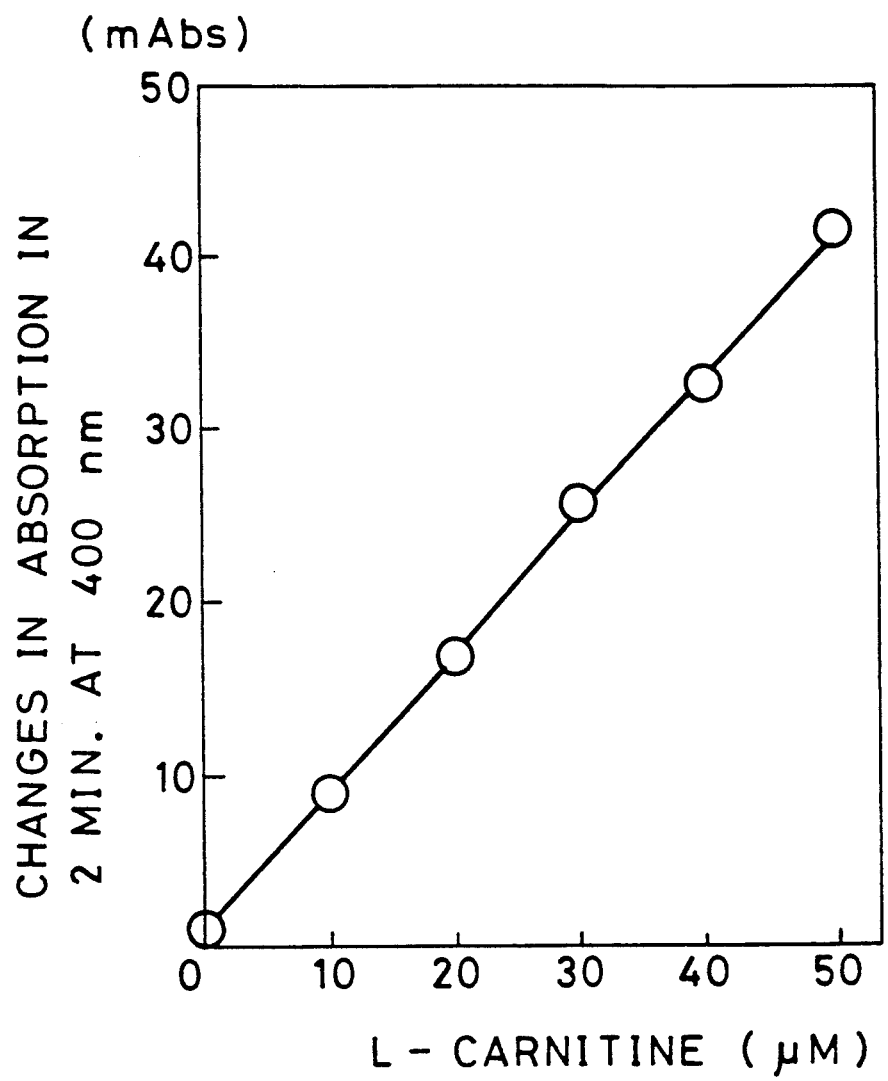
FIG. 1: rate assay on an amount of L-carnitine at 400 nm, as described in Example 1.

In the present invention, any type of L-carnitine dehydrogenase can be used that has the properties hereinabove. Examples of L-carnitine dehydrogenase suitable for use in the present invention are L-carnitine dehydrogenase produced by the following microorganisms.

*Pseudomonas aeruoinosa* A 7244 (NCTC) (*Eur. J. Biochem.*, Vol. 6, pp. 196-201 (1968), ibid., Vol. 10, pp. 56-60 (1969));

*Pseudomonas putida* IFP 206 (*Arch. Microbiol.*, Vol. 116, pp. 213-220, (1978), *Biochem. Biophys. Acta*, Vol. 957, pp. 335-339 (1988);

*Pseudomonas putida* ATCC 17633 (*Fresenius' Z. Anal. Chem.*, Vol. 320, pp. 285-289 (1985)); and

*Xanthomonas translucens* IFO 13558 (*Agr. Biol. Chem.*, Vol. 52, pp. 851-852 (1988)).

*Alcaligenes* sp. No. 981 FERM BP-2570 (product of Toyo Jozo Co., U.S. patent application Ser. No. 07/596,994).

Among these, L-carnitine dehydrogenase originated from *Alcaligenes* sp. No. 981 is preferable for its stability in buffer solution.

L-carnitine dehydrogenase originated from *Alcaligenes* sp. No. 981 is a novel L-carnitine dehydrogenase, which is produced, for example, by microorganisms of the genus *Alcaligenes* sp. No. 981 FERM BP-2570, isolated from a soil sample from a potato field in Gojo-shi, Nara prefecture, Japan.

The taxonomical properties of this strain are as follows:

A. Morphological properties:

Observations on a nutrient agar medium, cultured for 18-24 hours at 28°-30° C., are as follows:

Round edge with straight or slightly curved bacillus and single or double linked somewhat short chain. No formation of spores. Sizes are 0.4-0.6×1.2-2.5 μm. Peritrichal movement. No polymorphism.

B. Growth on various media:

Observations on various media, cultured for 18-24 hours at 28°-30° C., are as follows:

1. Nutrient agar slant medium: good growth with filiform. Wettish with luminescence. Ocherous but no formation of soluble pigment.
2. Nutrient agar plate medium: round, convex and whole round colonies. Smooth wettish surface. Ocherous or pale ocherous. No formation of soluble pigment.
3. Liquid medium (aqueous peptone): good growth with uniform turbidity. Formation of pellicle at long term (over 40 hours) culture.
4. BCP milk medium: alkaline after 4-5 days

| C. Physiological properties (+ = positive, (+) = weakly positive, − = negative) | |
| --- | --- |
| Gram-strain | − |
| KOH reaction | + |
| Capsule formation | − |
| Acid fastness stain | − |
| OF-test (Hugh Leifson) | No change |
| OF-test (nitrogen source: NH$_4$H$_2$PO$_4$) | 0 (oxidative) |
| Aerobic growth | + |
| Anaerobic growth | − |
| Growth temperature | |
| 41° C. | − |
| 37° C. | + |
| 15° C. | + |
| Halotolerant NaCl conc. % | |
| 0% | + |
| 5% | + |
| 7% | − |
| Growth pH | |
| pH 4.6 | − |
| pH 5.4 | + |
| pH 8.9 | + |
| pH 9.8 | − |
| Gelatin hydrolysis | − |
| Starch hydrolysis | − |
| Casein hydrolysis | − |
| Esculin hydrolysis | − |
| Cellulose hydrolysis | − |
| Tyrosine hydrolysis | − |
| Catalase production | + |
| Oxidase production | + |
| LV-reaction | − |
| Urease production (SSR) | − |
| Urease production (Chris) | − |
| Indol production | − |
| H$_2$S production (detection: lead acetate paper) | − |
| Acetoin production (K$_2$HPO$_4$) | − |
| Acetoin production (NaCl) | − |
| MR test | − |
| Nitrate reduction | |
| Gas detection | + |
| NO$_2^-$ | − |
| NO$_3^-$ | − |
| Utilization of Simmons medium | |
| Citrate | + |
| Malate | + |
| Maleate | − |
| Malonate | (+) |
| Propionate | − |
| Gluconate | − |
| Succinate | + |

| C. Physiological properties (+ = positive, (+) = weakly positive, − = negative) | |
| --- | --- |
| Utilization of Christenssen medium | |
| Citrate | + |
| Malate | + |
| Maleate | + |
| Malonate | + |
| Propionate | − |
| Gluconate | + |
| Succinate | + |
| Gas production from glucose | − |
| Acid formation from sugar | |
| Adonitol | − |
| L(+) arabinose | (+) |
| Cellobiose | − |
| Dulsitol | − |
| Meso-erythritol | − |
| Fructose | − |
| Galactose | + |
| Glucose | + |
| Glycerin | (+) |
| Inositol | − |
| Inulin | − |
| Lactose | − |
| Maltose | − |
| Mannitol | − |
| Mannose | + |
| Melezitose | − |
| Melibiose | − |
| Raffinose | − |
| L(+) rhamnose | − |
| D-ribose | − |
| Salicin | − |
| L-sorbose | − |
| Sorbitol | − |
| Starch | − |
| Saccharose | − |
| Xylose | − |
| Trehalose | − |
| Poly-β-hydroxybutyrate accumulation | − |

| D. Utilization of carbon sources:  Test medium: liquid medium (pH 7.0) containing carbon source 5 g, NaCl 5 g, MgSO$_4$.7H$_2$O 0.2 g, NH$_4$H$_2$PO$_4$ 1.0 g and distilled water 1 l. Results are as follows: | |
| --- | --- |
| Glucose | + |
| L(+) arabinose | − |
| Fructose | + |
| Mannitol | − |
| Mannose | + |
| Gluconate | + |
| Acetate | + |
| Adipate | − |
| Pimerate | + |
| Suberate | + |
| Tartrate | + |

According to the above taxonomical properties, the microorganism displays the specific characteristics of Gram negative bacillus, namely, it is peritrichal in movement, is catalase positive and oxidase positive, does not produce acid from glucose in Hugh-Leifson medium containing peptone, and promotes oxidative decomposition of glucose and acid formation. It displays no spore formation nor polymorphism, and is aerobic.

Among Gram-negative bacillus, there are three microorganism genera which are peritrichal in movement, namely Alcaligenes, Chromobacterium and Flavobacterium. Chromobacterium produces violet colored pigment, and Flavobacterium produces yellow colored pigment; however, the present strain does not produce pigment. Hence the present strain belongs to the genus Alcaligenes.

Taxonomic properties of Alcaligenes in comparison with those of the present strain, according to *Bergey's Manual of Systematic Bacteriology*, Vol. 1 (1984), are illustrated by comparing *Alcaligenes fatalist* (hereinafter designated F), *Alcaligenes denitrificans* (hereinafter designated D) and *Alcaligenes denitrificans subsp. xylosoxidans* (hereinafter designated X), as follows:
+ = positive probability over 90%;
− = negative probability over 90%; and
d = not identified as + or −.

| | F | D | X | The Present Strain |
| --- | --- | --- | --- | --- |
| Oxidase production | + | + | + | + |
| Nitrate reduction | − | + | + | + |
| Nitrite reduction | + | + | + | + |
| Gelatin hydrolysis | − | − | − | − |
| Acid fromation in OF-medium | | | | |
| Xylose | − | − | + | − |
| Glucose | − | − | + | − |
| Acid formation in peptone-free medium | | | | |
| Xylose | | | + | − |
| Glucose | | | + | + |
| Utilization of carbon sources | | | | |
| Glucose | − | − | + | + |
| L(+) arabinose | − | − | − | − |
| Fructose | − | − | d | + |
| Mannitol | − | − | − | − |
| Mannose | − | − | d | + |
| Gluconate | − | + | + | + |
| Acetate | + | + | + | + |

According to the above comparison, the present strain No. 981 has many identical properties with *Alcaligenes denitrificans subsp. xylosoxidans* but has specific differences as to acid formation in OF-medium and acid formation from xylose. Accordingly, the present strain has been designated Alcaligenes sp. No. 981 and has been deposited at The Fermentation Research Institute and assigned deposit No. FERM BP-2570.

In the enzymatic reaction hereinbelow illustrated, $A_1$ or $B_2$ is of the thio-NAD group or NAD group of coenzymes. Examples of the NAD group are nicotinamide adenine dinucleotide (NAD), acetylpyridine adenine dinucleotide (acetyl NAD), acetylpyridine hypoxanthine dinucleotide and nicotinamide hypoxanthine dinucleotide (deamino NAD). Examples of the thio-NAD group are thionicotinamide adenine dinucleotide (thio-NAD) and thionicotinamide hypoxanthine dinucleotide.

In the present invention, when $A_1$ is of the thio-NAD group, $B_1$ is of the NAD group, and when $A_1$ is of the NAD group, $B_1$ is of the thio-NADH group. Hence at least one will be a thio-type coenzyme.

$A_1$ and $B_1$ are used in excess as compared with L-carnitine and are in excess as compared with the Km-value of carnitine dehydrogenase for $A_1$ and $B_1$. Specifically a 200,000–10,000 times molar excess relative to carnitine is preferred.

In a composition for an assay of L-carnitine according to the present invention, the concentration of $A_1$ and $B_1$ is 0.02–100 mM, preferably 0.05–30 mM, and the concentration of L-carnitine dehydrogenase is 5–1000 U/ml, preferably 10–150 U/ml or more.

The L-carnitine dehydrogenase used in the composition for assay of L-carnitine according to the present invention can be an enzyme having reactivity on a substrate of L-carnitine together with a suitable coenzyme NAD or thio-NAD. Its suitability can be confirmed by using the said coenzyme and substrate. L-carnitine dehydrogenase produced by Alcaligenes sp. No. 981 (product of Toyo Jozo Co.) has a relative activity of approx. 15% when coenzyme thio-NAD is used, as compared to use of NAD. The Km-value of L-carnitine, NAD and thio-NAD under the same conditions is 9.3 mM, 0.14 mM and 0.40 mM, respectively.

In the composition of the reaction medium, two coenzymes are selected by considering the relative activity of L-carnitine dehydrogenase on each coenzyme. Thereafter, the pH condition thereof on each optimum pH of the forward reaction and reverse reaction is adjusted to set up the pH-condition wherein a ratio of reaction rate on the forward reaction and reverse reaction approaches 1.

In the present invention, L-carnitine dehydrogenase from a single origin or from plural origins can be used.

L-carnitine in a specimen can be assay by adding 0.001–0.5 ml of a specimen to the assay composition containing the above components (1) (3), reacting at 37° C., then measuring an amount of generated $A_2$ or consumed $B_1$ over an interval spanning two time points after staring the reaction, for example a minute between 3 mins. and 4 mins. after starting, or five minutes between 3 mins. and 8 mins. after starting the reaction. Measurement is effected by determining the changes of absorption at each optical absorption. Alternatively, the enzymatic reaction is stopped at a constant time after starting of the reaction, for example after 10 mins., then changes of absorption value can be measured. For example, when $A_2$ is thio-NADH and $B_1$ is NADH, generated $A_2$ is measured by an increase of absorption at 400 nm (molecular absorption coefficient: 11,200 $M^{-1}cm^{-1}$, Methods in Enzymology, Vol. 55, p. 261 (1979)) or consumed B is measured by a decrease of absorption at 340 nm (molecular absorption coefficient: 6200 $M^{-1}cm^{-1}$), and the thus-obtained value is compared with the value of a known concentration of reference L-carnitine, whereby a concentration of L-carnitine in a specimen can be measured in real time.

According to the assay method of the present invention, since L-carnitine itself existing in a specimen is introduced into the enzymatic cycling reaction, it is little affected by any coexisting substances in the specimens, and hence a measurement of a blank value of the specimen is not required. Thus, a simple assay system using a rate assay can be achieved.

In the present invention, measuring a value of $A_2$ or $B_1$ can be performed not only by absorbency, but also by other known enzymatic methods instead.

Further, according to the assay method of the present invention, there can be assayed not only free L-carnitine but also L-carnitine liberated from hydrolysis of acyl carnitine such as acetyl carnitine. L-carnitine per se in a specimen can be directly assay by the assay method of the present invention, without hydrolysis of the specimen. Thereafter, the total amount of L-carnitine and acylcarnitine can be assayed after hydrolyzing the specimen. The amount of acylcarnitine in the specimen can be obtained by subtracting the amount of L-carnitine found to be in the specimen without hydrolysis from the total amount of L-carnitine after hydrolyzing the acylcarnitine in the specimen.

Furthermore, a substrate in an enzymatic reaction system involving generation or consumption of L-carnitine, or an enzymatic activity thereof can also be assayed. Examples of these enzymatic systems are:

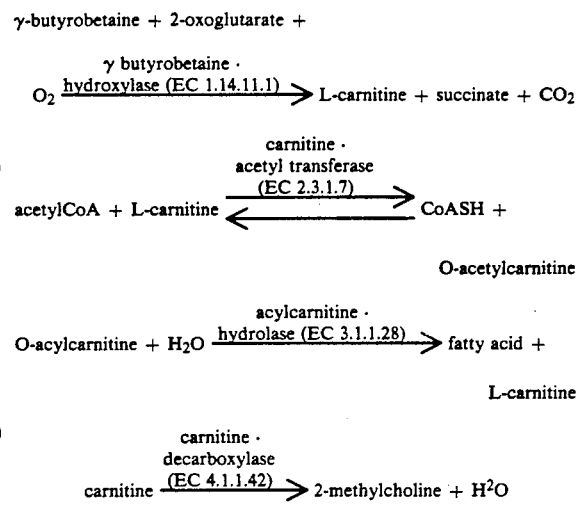

and in these systems, measurement of substrate or enzymatic activity can be achieved by the assay method of the present invention.

As explained above, the present invention has advantages in that no measurement error can occur, due to use of coenzymes each having a different absorption in its reduced form, and in that the amounts of free L-carnitine, total carnitine and acylcarnitine can also be assayed precisely and rapidly with even a small amount of specimen.

EXAMPLES

The following examples illustrate the present invention but are not to be construed as limiting.

REF. EXAMPLE 1

| (i) Culturing Alcaligenes sp. No. 981: | |
|---|---|
| DL carnitine hydrochloride (Sigma Chem. Co.) | 3.0% |
| KH$_2$PO$_4$ | 0.2% |
| K$_2$HPO$_4$ | 0.4% |
| MgSO$_4$.7H$_2$O | 0.05% |
| FeSO$_4$.7H$_2$O | 0.002% |
| MnSO$_4$.nH$_2$O | 0.001% |
| pH 7.0 | |

100 ml of a liquid medium comprising the above composition was sterilized in a 500 ml Erlenmeyer flask at 120° C. for 20 mins. One loopful of Alcaligenes sp. No. 981 was inoculated into the medium and the medium was cultured at 28° C. with stirring at 120 rpm for 40 hours to obtain the cultured mass (95 ml) (enzyme activity: 1.2 U/ml).

| (ii) DL-carnitine hydrochloride (Sigma Chem. Co.) | 3.0% |
|---|---|
| yeast extract (Kyokuto Seiyaku Co.) | 0.1% |
| K$_2$HPO$_4$ | 0.054% |
| KH$_2$PO$_4$ | 0.746% |
| MgSO$_4$.7H$_2$O | 0.05% |
| CaCl$_2$.2H$_2$O | 0.002% |
| FeSO$_4$.7H$_2$O (pH 7.0) | 0.002% |
| MnSO$_4$.nH$_2$O | 0.002% |
| disform CB 442 (Nihon Yushi Co.) | 1 ml/lit. |
| pH 7.0 | |

20 l of a liquid medium comprising the above composition was sterilized in a 30 l jar fermenter by heating. 90 ml of the pre-cultured seed culture obtained in step (i) above was inoculated therein and the mixture was cultured at 28° C., with aeration of 20 l/min., inner pressure 0.4 kg/cm², and agitation at 200 rpm for 27 hours to obtain the cultured mass (19 l) (enzyme activity: 3.0 U/ml).

REF. EXAMPLE 2

Purification of enzyme:

Bacterial cells collected by centrifugation from the cultured broth (19 l) obtained in Ref. Example 1, Culture (ii), were suspended in 40 mM Tris-HCl buffer (pH 8.0, 5 l) containing 0.1% lysozyme and 15 ml EDTA 2 Na and solubilized at 37° C. for 1 hour; then the mixture was centrifuged to remove precipitate and to obtain a supernatant solution (4500 ml) (activity: 10.3 U/ml). 1100 g ammonium sulfate was added to the supernatant solution, which was mixed well by stirring and then centrifuged to separate the precipitate. An additional 700 g ammonium sulfate was then added to the supernatant solution to dissolve the precipitate, and the solution was centrifuged to obtain a new precipitate. The new precipitate was dissolved in 40 mM Tri-HCl buffer (pH 8.0, 500 ml) (specific activity 84.1 U/ml), and the resultant solution was dialyzed against 40 mM Tris-HCl buffer (pH 8.0, 10 lit.) The dialyzed enzyme solution was charge don a column of DEAE Sepharose CL-6B (Pharmacia Co.) (200 ml) which was buffered with 40 mM Tris-HCl buffer (pH 8.0), washed with 40 mM Tris-HCl buffer containing 0.1M KCl, (pH 8.0, 1 lit.) and eluted with 40 mM Tris-HCl buffer containing 03M KCl (pH 8.0) to obtain an enzyme solution (300 ml, specific activity 120.5 U/ml). The enzyme solution was dialyzed against 40 mM Tris-HCl buffer (pH 8.0, 10 lit.) The dialyzed enzyme solution was charge don a column of hydroxylapatite (Koken Co., 100 ml), which was buffered with 40 mM Tris-HCl buffer, washed with 40 mM Tris-HCl buffer (pH 8.0, 200 ml), then eluted with 2 mM phosphate buffer (pH 7.0, 100 ml) to obtain enzyme solution (100 ml, specific activity 331 U/ml). The thus-obtained enzyme solution was dialyzed against 20 mM phosphate buffer (pH 7.5, 5 lit.) to obtain 95 ml of an enzyme solution having a specific activity of 331 U/ml. The yield was 67.8%.

The purified L-carnitine dehydrogenase was found to have an NADH oxidase activity of less than 0.0001 U.ml.

The L-carnitine dehydrogenase thus obtained has the following properties:

1. Enzyme action:

The enzyme catalyzes a reaction of L-carnitine and NAD+ to generate 3-dehydrocarnitine and NADH, as shown below.

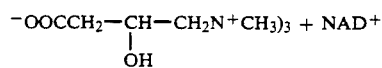

L-carnitine

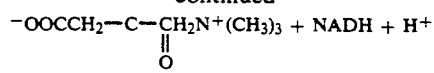

3-dehydrocarnitine

2. Substrate specificity:

| L-carnitine | 100% |
|---|---|
| Choline | 0 |
| Glycinebetaine | 0 |
| Glucose | 0 |
| Lysine | 0 |

3. Molecular weight:
51000±6000

Measured by TSK-gel G3000 SW (Toso Co., 0.75×60 cm)

Elution: 0.1M phosphate buffer (pH 7.0) containing 0.2M NaCl.

Standard: following molecular markers (Oriental Yeast Co.) are used.

| M.W. 12,400 | Cytochrome C |
|---|---|
| M.W. 32,000 | adenylate kinase |
| M.W. 67,000 | enolase |
| M.W. 142,000 | lactate dehydrogenase |
| M.W. 290,000 | glutamate dehydrogenase |

4. Isoelectric point:
pH 5.3±0.6

Measured by electrofocussing using carrier ampholite at 4° C., 700V, for 40 hours. The activity of a fraction of each enzyme is measured.

5. Km-value: 0.141 mM (NAD ), 9.3 mM (L-carnitine)

Km-value for NAD is measured in various concentrations of NAD* in a reaction mixture of:
100 mM Tris-HCl buffer (pH 9.0)
5U diaphorase (Toyo Jozo Co.)
0.025% NBT (Wako Pure Chem. Co.)
1% polyoxyethylene (20) sorbitan monooleate (80) (Wako Pure Chem. Co.) and
50 mM L-carnitine.

In the reaction mixture, 50 mM L-carnitine is replaced by 1 mM NAD , and the concentration of L-carnitine is varied to measure the Km-value of L-carnitine.

The results are as shown above.

6. Heat stability:

The enzyme, dissolved in 20 mM Tris-HCl buffer (pH 8.0), to produce a 1.00 U/ml solution, is incubated for one hour at various temperatures, and the residual activity is measured.

The results show that the enzyme is stable up to 45° C.

7. Optimum temperature:

The enzyme activity is measured at 35°, 40°, 45°, 50°, 55° and 60° C., respectively, in 100 mM Tris-HCl buffer (pH 9.0) according to the assay method illustrated hereinafter. The reaction was stopped in each case after 10 mins. incubation by adding 0.1N HCl (2 ml), whereupon the optical absorption was measured at 550 nm. The enzyme shows maximum activity at 50° C.

8. pH-stability:

The residual activity of the enzyme (1 U/ml, 40 mM buffer solution) is measured in various buffer solutions, i.e. acetate buffer, pH 5.6-6.0; phosphate buffer, pH 6.0-8.0; Tris-HCl buffer, pH 8.0-9.0 and glycine-NaOH buffer, pH 9.0-10, after heating at 45° C. for 30 mins. The enzyme is stable at pH 8.0-9.0 with a residual activity of over 95%.

9. Optimum pH:

In an assay method for enzyme activity as illustrated hereinafter, 100 mM Tris-HCl buffer in the reaction mixture is replaced by 100 mM phosphate buffer (pH 6.5-7.5), 100 mM Tris-HCl buffer (pH 8.0-9.0) and 100 mM glycine-NaOH buffer (pH 9.0-10.0), and incubated at 37° C. for 10 mins. The reaction was stopped in each case by adding 0.1N HCl (2 ml), whereupon the absorption at 550 nm was measured. A maximum activity is observed at approx. pH 9.0.

10. Long-term stability in aqueous solution:

Stability of L-carnitine dehydrogenase combined with 0.05 mM NAD is measured in 50 mM Tris-HCl buffer (pH 9.0, 10 U/ml) at 5° C. after two weeks storage.

L-carnitine dehydrogenase of the present invention has a residual activity of 96% after one week and 82% after two weeks, thus showing superior stability.

11. Assay method of L-carnitine dehydrogenase activity:

(1) Reaction mixture:
50 mM Tris-HCl buffer (pH 9.0)
1 mM NAD*
5 U Diaphorase (Toyo Jozo Co.)
0.05% NBT (Wako Pure Chem. Co.)
100 mM KCl
0.5% polyoxyethylene (20) sorbitan monooleate (80) (Wako Pure Chem. Co.)
100 mM L-carnitine (Sigma Chem. Co.)

(2) Enzyme Assay:

The above reaction mixture (1 ml) is incubated in a small test tube at 37° C. for 5 mins. Dilute enzyme solution (0.02 ml) is added and stirred to initiate the reaction. After exactly 10 mins., 0.1N HCl (2.0 ml) was added and stirred to stop the reaction. Absorption at 550 nm ($A_{550}$ nm) is measured to obtain absorption $A_1$. The assay was repeated using the above reaction mixture except that L-carnitine was not included. The mixture is also treated in the same manner as described above and its absorption Ao was measured.

3) Calculation of enzyme activity:

$$U/ml = \frac{(A_1 - Ao)}{21.7} \times \frac{1}{10} \times \frac{3.02}{0.02} \times Z$$

wherein
21.7: molecular absorption coefficient cm²/μmol
Z: dilution ratio

EXAMPLE 1

Reagents:
100 mM Tris-HCl buffer (pH 9.5)
5 mM Thio-NAD (Sankyo Co.)
0.2 mM NADH (Oriental Yeast Co.)
92 U/ml L-carnitine dehydrogenase (obtained from Ref. Example 2)

Procedure:

The above reagent mixture (1 ml) was put into cuvettes and 0.05 ml of each of a range of concentrations of L-carnitine solution (0, 10, 20, 30, 40 and 50 μM, respectively) was added thereto, with the reaction temperature at 37° C. After incubation commenced, a difference in absorbance at 3 mins. and 5 mins. was measured. The results are shown in FIG. 1, from which it can be seen that a linear relation between the amount of L-carnitine and the change in absorption was observed.

EXAMPLE 2

Figure 2:
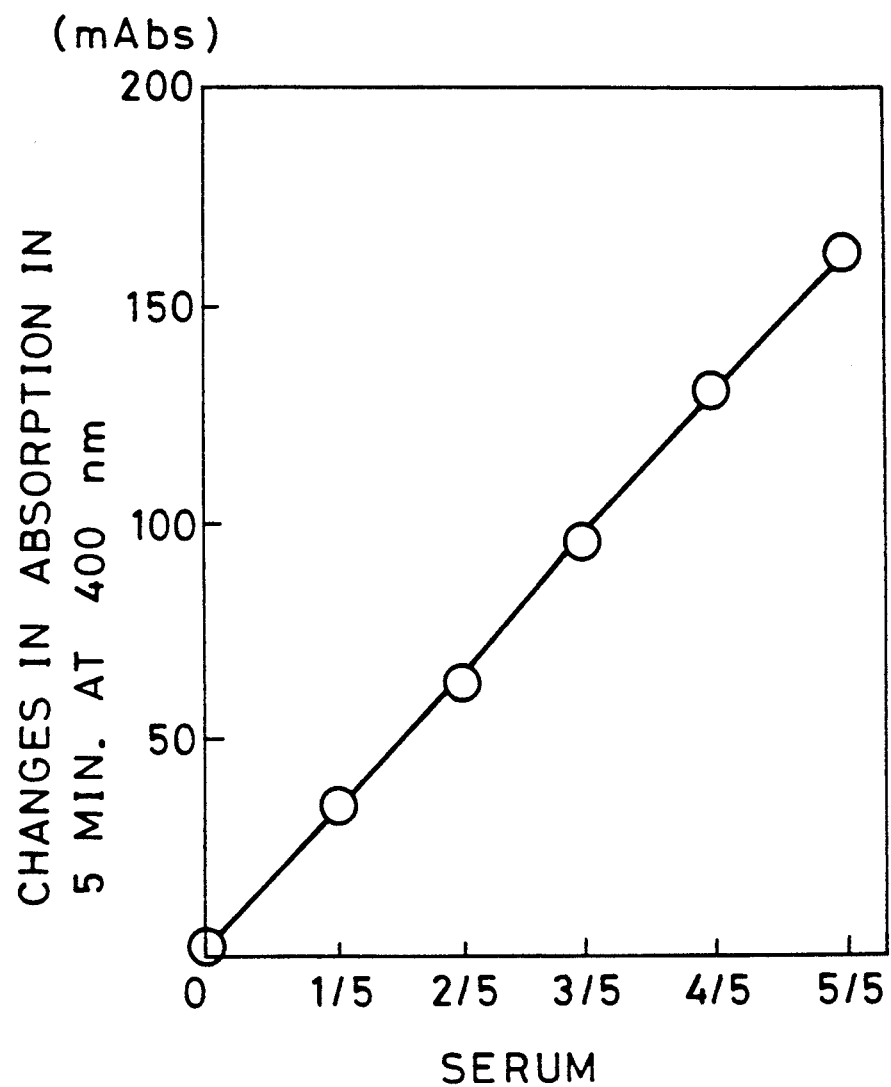
FIG. 2: rate assay of an amount of serum at 400 nm, as described in Example 2.

Reagents:
40 mM Glycine.NaOH buffer (pH 10.0)
5 mM Thio-NAD (Sankyo Co.)
0.5 mM NADH (Oriental Yeast Co.)
0.5% Polyoxyethylene (20) sorbitan monooleate (80) (Wako Pure Chem. Co.)
120 U/ml L-carnitine dehydrogenase (obtained from Ref. Example 2)
2 mM Oxamic acid Procedure:

The above reagent mixture (1 ml) was put into a cuvette. A five-fold dilution of normal serum (each 50 μl) was added thereto, followed by incubation at 37° C. After the reaction started, the absorbance at 400 nm was measured at 1 min. and 6 mins. The difference of absorbance at 1 min. and 6 mins. is shown in FIG. 2.

A 50 μM L-carnitine solution (50 μl) was also treated in the same manner as described above. Then L-carnitine in the normal serum was calculated and was found to be 54.3 μM.

EXAMPLE 3

Reagents:
40 mM Glycine.NaOH buffer (pH 10.0)
5 mM Thio-NAD (Sankyo Co.)
0.5 mM NADH (Oriental Yeast Co.)
0.5% Polyoxyethylene (20) sorbitan monooleate (80) (Wako Pure Chem. Co.)
120 U/ml L-carnitine dehydrogenase (obtained from Ref. Example 2)
2 mM Oxamic acid Procedure:

The above reagent mixture (1 ml) was put into cuvettes. A series of 50 μl specimens (50 μl), comprising L-carnitine added to normal serum in concentrations of 10, 20 and 50 μM, was treated in the same manner as described in Example 2. The results are shown in Table 1, where yield is observed as 97.0-102.0%

TABLE 1

| Amount Added (μM) | Observed (μM) | Difference (μM) | Yield (%) |
|---|---|---|---|
| 0 | 54.3 | — | — |
| 10 | 64.5 | 10.2 | 102.0 |
| 20 | 74.2 | 19.9 | 99.5 |
| 50 | 103.3 | 48.5 | 97.0 |

EXAMPLE 4

Reagents:
40 mM Glycine.NaOH buffer (pH 10.0)
5 mM Thio-NAD (Sankyo Co.)
0.2 mM NADH (Oriental Yeast Co.)
0.5% Polyoxyethylene (20) sorbitan monooleate (80) (Wako Pure Chem. Co.)
100 U/ml L-carnitine dehydrogenase (obtained from Ref. Example 2)

2 mM Oxamic acid

Procedure:

2 mM Tris-HCl buffer (0.025 ml) and 1N KOH (0.025 ml) were added to serum (0.05 ml). Acylcarnitine in the serum was hydrolyzed by incubating at 37° C. for one hour. Thereafter the reaction mixture was neutralized by adding 2.5N HCl (0.05 ml) to prepare a specimen for total carnitine assay. A mixture of serum (0.05 ml) and physiological saline (0.1 ml) was prepared as a specimen for free carnitine assay.

the above reagent mixture was put into cuvettes (1 ml each), and 0.05 ml of a specimen as prepared above was added to each cuvette, then incubated at 37° C. After reaction was started, a difference at 1 min. and 6 mins. in absorption at 400 nm was measured.

L-carnitine of known concentration was treated in the same manner as above, and amounts of total carnitine and free carnitine were calculated from the observed value. Then, an amount of acylcarnitine was measured from the difference between the amounts of total and free carnitine.

In Table 2, the results obtained from three different serums are shown.

TABLE 2

|  | Total Carnitine (μM) | Free Carnitine (μM) | Acylcarnitine (μM) |
| --- | --- | --- | --- |
| Serum 1 | 84.5 | 35.3 | 49.2 |
| Serum 2 | 50.0 | 26.3 | 23.7 |
| Serum 3 | 89.5 | 43.2 | 46.3 |

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. A method of assaying L-carnitine comprising reacting a specimen containing L-carnitine with the following reagents:

a) L-carnitine dehydrogenase having coenzymes of thionicotinamide adenine dinucleotide group (thio-NAD group) and nicotinamide adenine dinucleotide group (NAD group), and which catalyzes a reversible reaction forming dehydrocarnitine from a substrate of L-carnitine;

b) $A_1$;

c) $B_1$;

to effect a cycling reaction of the formula

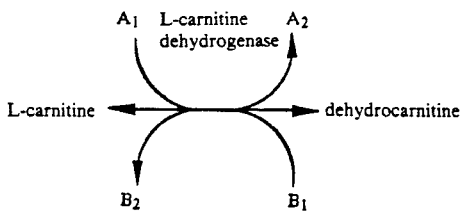

wherein $A_1$ is thio-NAD group or NAD group, $A_2$ is a reduced form of $A_1$, when $A_1$ is thio-NAD group, $B_1$ is reduced NAD group and when $A_1$ is NAD group, $B_1$ is reduced thio-NAD, and wherein $B_2$ is an oxidized form of $B_1$; and measuring an amount of $A_2$ or $B_1$ generated or consumed by the cycling reaction.

2. The assay method according to claim 1, wherein said L-carnitine dehydrogenase is generated by a microorganism of the genus Alcaligenes.

3. The assay method according to claim 1, wherein said NAD group is selected from the group consisting of nicotinamide adenine dinucleotide (NAD), acetylpyridine adenine dinucleotide (acetyl NAD), acetylpyridine hypoxanthine dinucleotide and nicotinamide hypoxanthine dinucleotide (deamino-NAD).

4. The assay method according to claim 1, wherein said thio-NAD group is thionicotinamide adenine dinucleotide (thio-NAD) or thionicotinamide hypoxanthine dinucleotide.

5. The assay method according to claim 2, wherein said microorganism of the genus Alcaligenes is *Alcaligenes sp.* No. 981.

6. A composition for assaying L-carnitine, comprising:

a) L-carnitine dehydrogenase having coenzymes of thionicotinamide adenine dinucleotide group (thio-NAD group) and nicotinamide adenine dinucleotide group (NAD group), and which catalyzes a reversible reaction forming dehydrocarnitine from a substrate of L-carnitine;

b) $A_1$;

c) $B_1$;

wherein $A_1$ is thio-NAD group or NAD group, when $A_1$ is thio-NAD group, $B_1$ is reduced form of NAD group, and when $A_1$ is NAD group, $B_1$ is reduced form of thio-NAD group.

7. The composition according to claim 6, wherein said NAD group is selected from the group consisting of nicotinamide adenine dinucleotide (NAD), acetylpyridine adenine dinucleotide (acetyl NAD), acetylpyridine hypoxanthine dinucleotide and nicotinamide hypoxanthine dinucleotide (deamino-NAD).

8. The composition according to claim 6, wherein said thio-NAD group is thionicotinamide adenine dinucleotide (thio-NAD) or thionicotinamide hypoxanthine dinucleotide.

9. The composition according to claim 6, wherein said L-carnitine dehydrogenase is generated by a microorganism of the genus Alcaligenes.

10. The composition according to claim 9, wherein said microorganism of the genus Alcaligenes is *Alcaligenes sp. No.* 981.

* * * * *